US010016563B2

(12) United States Patent
Horiuchi et al.

(10) Patent No.: US 10,016,563 B2
(45) Date of Patent: Jul. 10, 2018

(54) BARREL FOR SYRINGE AND PRE-FILLED SYRINGE

(71) Applicant: Terumo Kabushiki Kaisha, Tokyo (JP)

(72) Inventors: Aiko Horiuchi, Kanagawa (JP);
Tomoyuki Hojo, Kanagawa (JP);
Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/061,620

(22) Filed: Mar. 4, 2016

(65) Prior Publication Data
US 2016/0184522 A1 Jun. 30, 2016

Related U.S. Application Data

(63) Continuation of application No. PCT/JP2014/073177, filed on Sep. 3, 2014.

(30) Foreign Application Priority Data

Sep. 6, 2013 (JP) .................................. 2013-185531

(51) Int. Cl.
*A61M 5/32* (2006.01)
*A61M 5/28* (2006.01)
(Continued)

(52) U.S. Cl.
CPC ............ *A61M 5/28* (2013.01); *A61M 5/3129* (2013.01); *A61M 5/3135* (2013.01);
(Continued)

(58) Field of Classification Search
CPC .. A61M 2005/3104; A61M 2005/3106; A61M 2005/3118; A61M 5/3134; A61M 5/345
(Continued)

(56) References Cited

U.S. PATENT DOCUMENTS 5,954,657 A * 9/1999 Rados .................... A61M 39/20
600/486
2004/0087906 A1* 5/2004 Henderson .......... A61M 5/3134
604/187

FOREIGN PATENT DOCUMENTS

JP   H10-502558 A   3/1998
JP   2004-283465 A  10/2004
(Continued)

OTHER PUBLICATIONS

International Search Report for PCT/JP2014/073177 dated Nov. 25, 2014.

*Primary Examiner* — Phillip Gray
(74) *Attorney, Agent, or Firm* — Foley & Lardner LLP

(57) ABSTRACT

A syringe barrel includes an barrel main body having a female luer at a distal end of the barrel main body, the female luer being configured such that a male luer is insertable into and connectable to the female luer; and a cap that is detachably attached to the female luer to close an opening of the female luer. The female luer has a female luer-side connector, and the cap is detachably attached to the female luer via the female luer-side connector. The cap includes an insertion part inserted into the female luer, a sealing part that seals the opening of the female luer, and a cap-side connector that is detachably engaged with the female luer-side connector.

14 Claims, 8 Drawing Sheets

(51) Int. Cl.
  *A61M 5/315* (2006.01)
  *A61M 39/20* (2006.01)
  *A61M 5/31* (2006.01)

(52) U.S. Cl.
  CPC ........ *A61M 5/31505* (2013.01); *A61M 39/20* (2013.01); *A61M 2005/3104* (2013.01); *A61M 2005/3106* (2013.01)

(58) Field of Classification Search
  USPC ....................................................... 604/199
  See application file for complete search history.

(56) References Cited

FOREIGN PATENT DOCUMENTS

| | | |
|---|---|---|
| JP | 4156791 B2 | 9/2008 |
| JP | 2009-240684 A | 10/2009 |
| JP | 2012-528689 A | 11/2012 |
| WO | WO-96/02291 A1 | 2/1996 |
| WO | WO-2010/141508 A1 | 12/2010 |

\* cited by examiner

BARREL FOR SYRINGE AND PRE-FILLED SYRINGE

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2014/073177, filed on Sep. 3, 2014, which claims priority to Japanese Patent Application No. JP2013-185531, filed on Sep. 6, 2013. The contents of these applications are hereby incorporated by reference in their entireties.

BACKGROUND

The present disclosure relates to a syringe barrel and a pre-filled syringe.

One type of known conventional syringe is a pre-filled syringe that has previously been filled with a liquid drug or the like (see, for example, Japanese Patent No. 4156791). It is important that the liquid drug or the like contained in the pre-filled syringe is prevented from leaking through a distal end opening of the syringe before its use, particularly during transport. Therefore, a cap is attached to the syringe barrel of the pre-filled syringe to seal the cylinder tip (syringe distal end opening) of the main body of the barrel in a liquid-tight manner.

One example of such a pre-filled syringe has a female luer (female fitting part) configured as the cylinder tip of the barrel main body. The pre-filled syringe having a female luer (FM syringe) is connected to, for example, a pre-filled syringe that has a male luer (male fitting part) provided at its distal end (ML syringe), the ML syringe having been previously filled with a liquid (e.g., normal saline). Then, in a state where the FM syringe is connected to the ML syringe, the liquid drug in the FM syringe is sucked into the ML syringe and mixed with the liquid within the ML syringe to prepare a desired liquid drug.

The pre-filled syringe having a female luer has a cap attached to the female luer, and the cap has a sealing part made of an elastic material. In order to prevent the occurrence of liquid leakage when a male luer is connected, the sealing part is configured so that part of the sealing part corresponding to the volume of the male luer to be inserted is inserted into the female luer in a state where the cap is attached to the female luer. Further, the sealing part has an outer periphery that is in close contact with the inner periphery of the female luer to provide liquid sealing performance.

SUMMARY OF THE INVENTION

In the process of producing the pre-filled syringe having a female luer, sterilization (high-pressure steam sterilization) is performed to achieve a predetermined cleanliness level. In terms of production, performing high-pressure steam sterilization in a state where the cap is attached to the female luer of the barrel main body is efficient. In this case, however, the inner periphery of the female luer cannot be sterilized because the sealing part of the cap is in close contact with the inner periphery of the female luer.

In consideration of such a problem, it is an object of certain embodiments of the present invention to provide a syringe barrel and a pre-filled syringe that can ensure liquid tightness at the time when a cap is not opened, can prevent the leakage of a drug at the time when a male luer is connected, and can sterilize the inner periphery of a female luer.

In order to achieve the above object, one embodiment of the present invention is directed to a syringe barrel including: an barrel main body having a female luer at a distal end of the barrel main body, the female luer being configured that a male luer is insertable into and connectable to the female luer; and a cap that is detachably attached to the female luer to close an opening of the female luer, wherein the female luer has a female luer-side connector that detachably fixes the cap, wherein the cap has an insertion part inserted into the female luer, a sealing part that seals the opening of the female luer, and a cap-side connector that is detachably engaged with the female luer-side connector, and wherein in a state where the cap is fixed to the female luer by engagement between the female luer-side connector and the cap-side connector, the insertion part is spaced apart from an inner periphery of the female luer, and the sealing part is in close contact with a distal end surface of the female luer along an entire circumference of the opening.

The syringe barrel has a gap provided between the inner periphery of the female luer and the insertion part, which makes it possible to sterilize the inner periphery of the female luer in its production process. More specifically, when the syringe barrel is subjected to sterilization in its production process, high-temperature steam or liquid is in contact with the inner periphery of the female luer, which makes it possible to sterilize the inner periphery. Further, the insertion part of the cap is inserted into the female luer, which makes it possible to prevent the leakage of a drug at the time when a male luer is connected. Further, according to an embodiment of the present invention, the opening of the female luer is liquid-tightly sealed not by close contact between the inner periphery of the female luer and the outer periphery of the insertion part but by close contact between the sealing part and the distal end surface of the female luer along the entire circumference of the opening. Therefore, the syringe barrel according to one embodiment of the present invention can help to ensure liquid tightness at the time when the cap is not opened, can help to prevent the leakage of a drug at the time when a male luer is connected, and can allow for sterilization the inner periphery of the female luer.

In the syringe barrel, the cap may have an elastic member having the sealing part, and a main body that supports the elastic member, has the cap-side connector, and is harder than the elastic member. A pressing part may be formed at a distal end of the female luer so as to project in a distal direction to press the sealing part along the entire circumference of the opening in a state where the cap is fixed to the female luer. In this case, the pressing part presses the sealing part along the entire circumference of the opening, and therefore the pressing part and the sealing part are in sufficiently close contact with each other so that excellent sealing performance is achieved.

In the syringe barrel, the elastic member may have a cylindrical part that has a closed proximal end and constitutes the insertion part, and a flange part that surrounds a distal end opening of the cylindrical part and constitutes the sealing part. In this case, the insertion part and the sealing part are integrally molded, and therefore only one portion is required to be sealed, and excellent sealing performance can be achieved by a simple structure.

In the above syringe barrel, the female luer-side connector and the cap-side connector may be threadedly engageable with each other.

In the above syringe barrel, the main body may have an anti-rotation part that prevents relative rotation of the elastic member with respect to the main body. This structure makes it possible to, when the cap is rotated to be removed from the female luer, prevent the elastic member from remaining on the female luer side due to sticking to the pressing part.

In the above syringe barrel, the anti-rotation part may be inserted into the cylindrical part and engaged with an inner periphery of the cylindrical part. In this case, the relative rotation of the elastic member with respect to the main body can be effectively prevented by a simple structure, and in addition, the elastic member can be stably supported by the anti-rotation part.

In the above syringe barrel, the anti-rotation part may have a columnar part that extends along an axial direction of the cap and a rib that projects from an outer periphery of the columnar part outward and extends in the axial direction. This structure makes it possible to more effectively prevent the relative rotation of the elastic member with respect to the main body.

In the above syringe barrel, the main body may have a cap-side engagement part, and the female luer may have a female luer-side engagement part that is engaged with the cap-side engagement part to prevent loosening of the cap in a state where the female luer-side connector and the cap-side connector are threadedly engaged with each other. This structure makes it possible to prevent the loosening of the cap.

In the above syringe barrel, an engagement force between the cap-side engagement part and the female luer-side engagement part may be larger than a disengagement force exerted on the cap based on an elastic force of the elastic member. This structure makes it possible to reliably prevent the loosening of the cap.

In the above syringe barrel, the main body may have a cylindrical cover that covers an outer periphery of the female luer, the cap-side engagement part may be formed at a proximal end part of the cover, and the female luer may have a projection that is formed to radially project from a outer periphery of a proximal end part of the female luer to constitute the female luer-side engagement part. This structure makes it possible to easily open the cap because engagement between the projection and the cover is released only by slightly rotating the cap.

In the above syringe barrel, a proximal-side inner periphery of the cover may have a reduced radius portion that constitutes the cap-side engagement part, wherein a distance from a rotation axis of the cap to the reduced radius portion at the time when the cap is threadedly engaged with the female luer is smaller than a distance from the rotation axis to an outer end of the projection, wherein the reduced radius portion of the cover is formed in a production process of the syringe barrel by expanding part of the proximal-side inner periphery of the cover outwardly by the projection and thereby deforming other part of the proximal-side inner periphery inwardly, and is engaged with the projection to prevent loosening of the cap in a state where the cap is attached to the female luer. In this case, the reduced radius portion of the cover that is engaged with the projection to prevent the loosening of the cap is obtained as a result of deformation of the proximal-side inner periphery caused by a force received from the projection, and therefore the projection and the cover establish an accurate positional relationship when engaged with each other. Therefore, it is not necessary to align a threaded engagement structure between the cap and the cylinder tip with the projection, and therefore it is possible to easily obtain a rattle-free structure for preventing the loosening of the cap.

In another embodiment, a pre-filled syringe includes the syringe barrel, a gasket that is liquid-tightly and slidably movable in the barrel main body, and a drug filled in a filling chamber defined by the barrel main body, the gasket, and the cap.

The syringe barrel and the pre-filled syringe according to certain embodiments of the present invention can ensure liquid tightness at the time when the cap is not opened, can prevent the leakage of a drug at the time when a male luer is connected, and can sterilize the inner periphery of the female luer.

DETAILED DESCRIPTION

Herein below, a syringe barrel and a pre-filled syringe according to embodiments of the present invention will be described with reference to the accompanying drawings.

Figure 1:
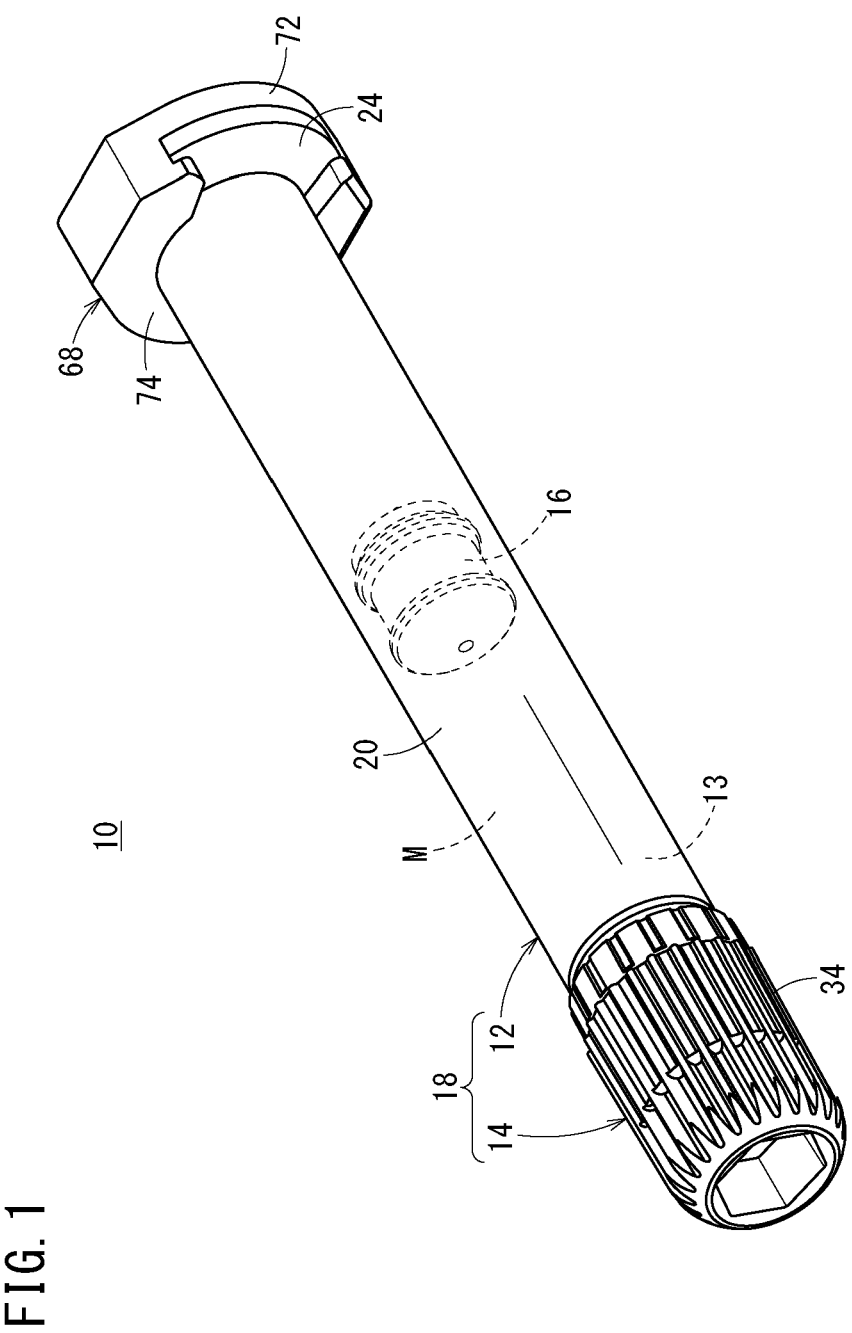
FIG. 1 is a perspective view of a pre-filled syringe according to one embodiment of the present invention.
Figure 2:
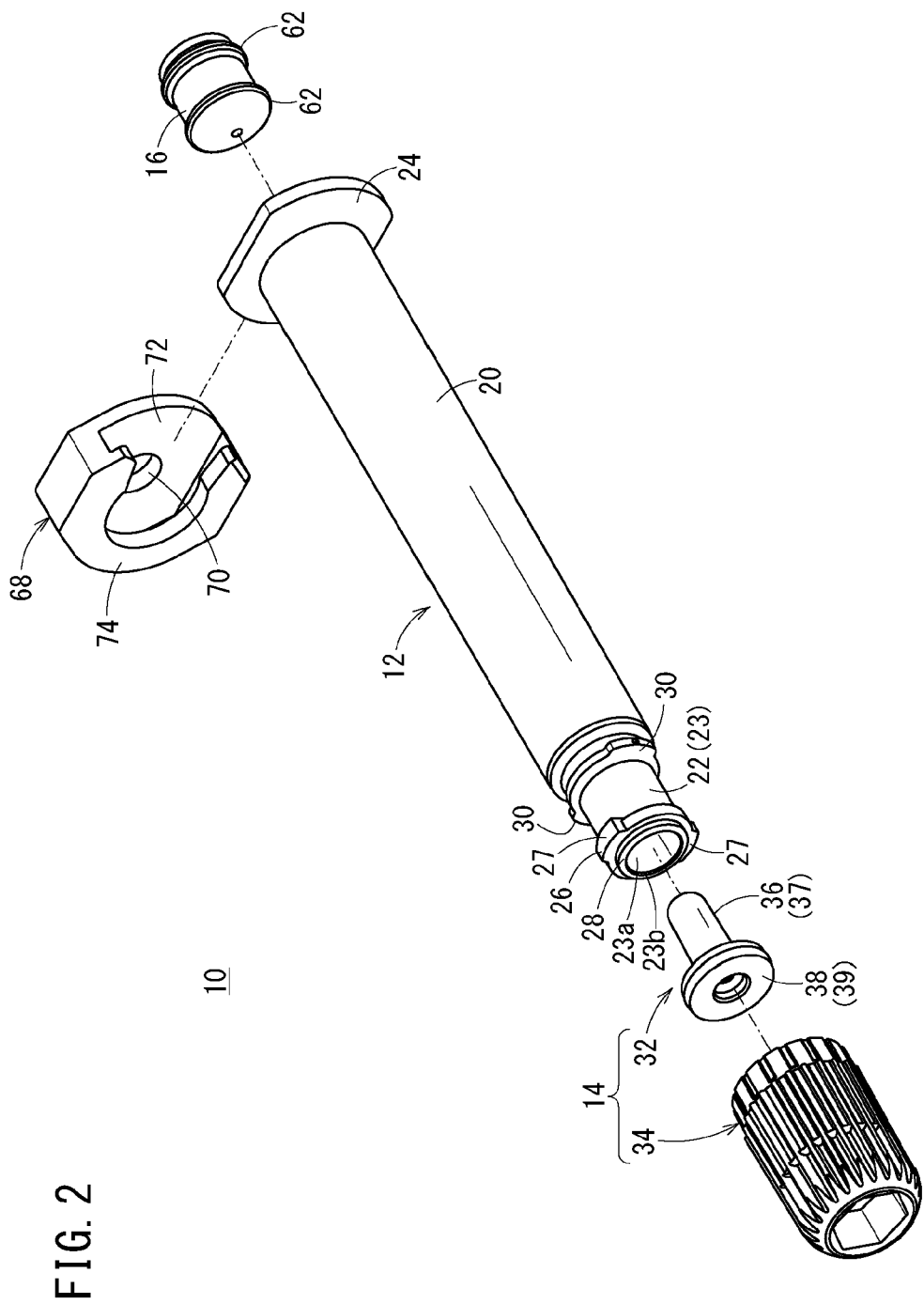
FIG. 2 is an exploded perspective view of the pre-filled syringe shown in FIG. 1.
Figure 3:
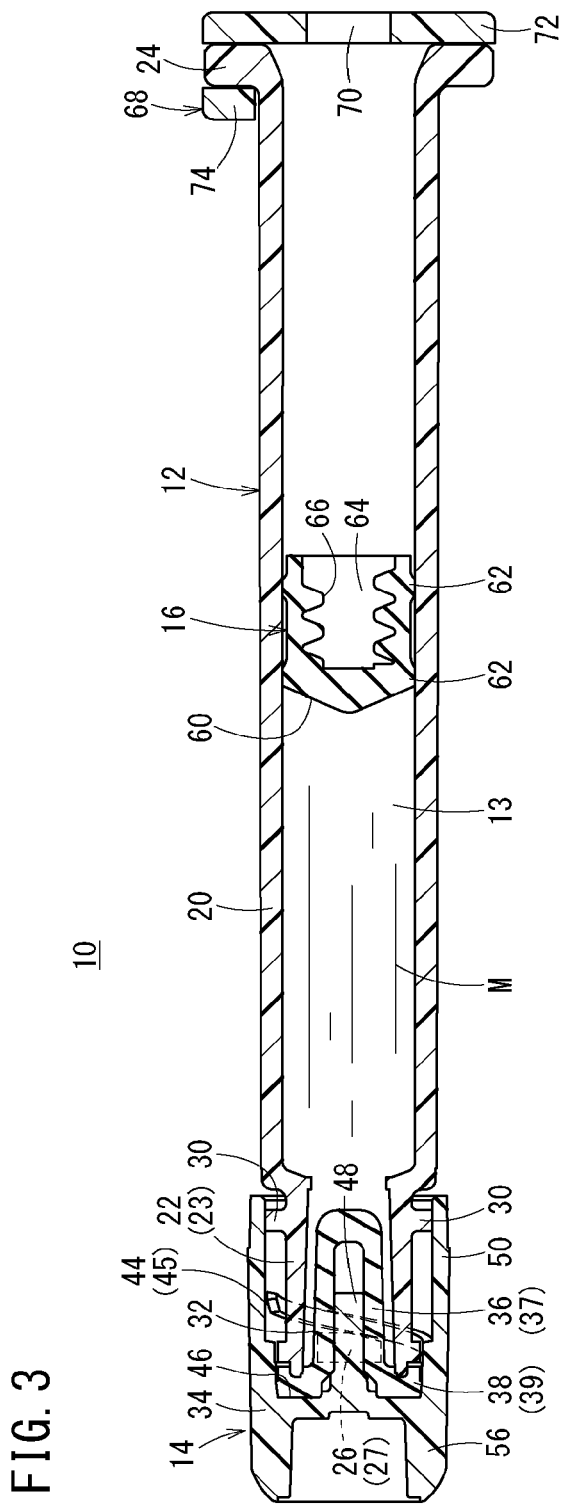
FIG. 3 is a longitudinal sectional view of the pre-filled syringe shown in FIG. 1.
Figure 4:
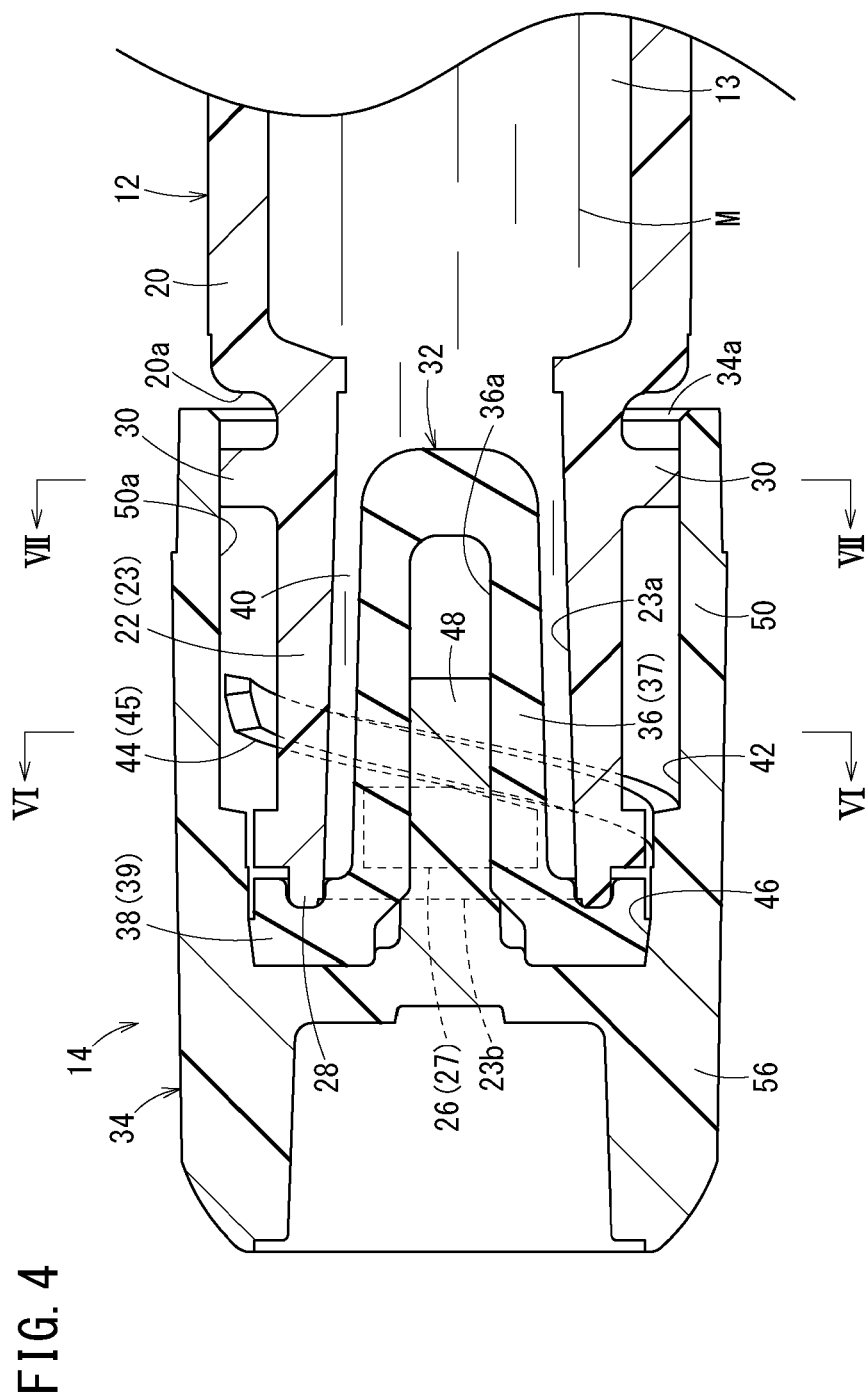
FIG. 4 is a partially-enlarged view of FIG. 3.

FIG. 1 is a perspective view of a pre-filled syringe 10 according to one embodiment of the present invention. FIG. 2 is an exploded perspective view of the pre-filled syringe 10. FIG. 3 is a longitudinal sectional view of the pre-filled syringe 10. FIG. 4 is an enlarged longitudinal sectional view of the distal end of the pre-filled syringe 10.

The pre-filled syringe 10 includes, as its main components, a cylindrical barrel main body 12 having a cylinder tip 22, a cap 14 that seals the cylinder tip 22 of the barrel main body 12, a gasket 16 that is liquid-tightly and slidably movable in the barrel main body 12, and a drug M filled in a filling chamber 13 formed in the barrel main body 12. In this pre-filled syringe 10, the barrel main body 12 and the cap 14 constitute a syringe barrel 18.

As shown in FIG. 2 and FIG. 3, the barrel main body 12 has a body part 20 constituting the main part of the barrel main body 12, a cylinder tip 22 provided at the distal end of the body part 20, and a flange 24 formed to radially project outward from the proximal end of the body part 20. The cylinder tip 22 projects from the distal end of the barrel main body 12 in the distal direction so as to have a diameter smaller than that of the barrel main body 12. The cylinder tip 22 constitutes a female luer 23 into and to which a male luer 82 can be inserted and connected (see FIG. 8B). The female luer 23 has a tapered inner periphery 23a (see FIG. 4) whose inner diameter increases toward the distal direction.

As shown in FIG. 2, on the distal-side outer periphery of the female luer 23, a female luer-side connector 26 is provided to detachably fix the cap 14. In this embodiment, the female luer-side connector 26 is a threaded engagement part (male screw) that is threadedly engageable with the cap 14. Specifically, the female luer-side connector 26 shown in the drawings includes two engagement projections 27 that project in opposite directions with respect to the axis of the barrel main body 12. Further, at the distal end of the female luer 23, a ring-shaped pressing part 28 is provided which projects in the distal direction and extends in the circumferential direction around the axis of the barrel main body 12. The pressing part 28 presses a sealing part 39 that will be described later along the entire circumference of an opening 23b in a state where the cap 14 is fixed (attached) to the female luer 23.

On the outer periphery of a proximal end part of the female luer 23, a projection 30 is provided to prevent the loosening of the cap 14 before use. In this embodiment, a pair of projections 30 is provided which projects in opposite directions with respect to the axis of the barrel main body 12. In a state where the cap 14 is fixed to the female luer 23, the projections 30 are engaged with a cap-side engagement part 51 in a proximal-side inner periphery 50a of a cover 50 that will be described later (see FIG. 7). In this way, the projections 30 prevent the loosening of threaded engagement between the cap 14 and the female luer 23. That is, the projections 30 constitute a female luer-side engagement part 31 that is engaged with the cap-side engagement part 51 to prevent the loosening of the cap 14 in a state where the female luer-side connector 26 and a cap-side connector 44 are threadedly engaged with each other. It is to be noted that the function of the projection 30 to prevent the loosening of the cap 14 will be described again after description of the specific structure of the cap 14. The projections 30 are provided near the proximal end of the female luer 23, that is, provided at a position slightly spaced apart from a distal end surface 20a of the body part 20 in the distal direction (see FIG. 4).

Examples of a constituent material of the barrel main body 12 having such a structure as described above include various resins such as polypropylene, polyethylene, polystyrene, polyamide, polycarbonate, polyvinyl chloride, poly-(4-methylpentene-1), acrylic resins, acrylonitrile-butadiene-styrene copolymers, polyesters such as polyethylene terephthalate, and cyclic polyolefins. Among them, resins such as polypropylene and cyclic polyolefins are preferred for ease of molding and heat resistance.

Next, the structure of the cap 14 detachably attached to the female luer 23 will be described. As shown in FIGS. 2 to 4, the cap 14 has an elastic member 32 that seals the opening 23b of the female luer 23, and a main body 34 that supports the elastic member 32. In a state where the cap 14 is attached to the female luer 23 before use, the opening 23b of the female luer 23 is liquid-tightly sealed with the cap 14 (see FIG. 2) so that the drug M does not leak through the opening 23b.

The elastic member 32 is placed in the main body 34 (in a recess 42 that will be described later). The elastic member 32 has a cylindrical part 36 that has an open distal end and a closed proximal end and extends in the axial direction of the cap 14, and a flange part 38 that surrounds the distal end opening of the cylindrical part 36 and radially projects outward. The elastic member 32 is formed by integrally molding the cylindrical part 36 and the flange part 38 without gap between them. The cylindrical part 36 constitutes an insertion part 37 inserted into the female luer 23. The flange part 38 constitutes a sealing part 39 that seals the opening 23b of the female luer 23.

Examples of a constituent material of the elastic member 32 include: various rubber materials such as natural rubber, butyl rubber, isoprene rubber, butadiene rubber, styrene-butadiene rubber, and silicone rubber; various thermoplastic elastomers such as polyurethane-based thermoplastic elastomers, polyester-based thermoplastic elastomers, polyamide-based thermoplastic elastomers, olefin-based thermoplastic elastomers, and styrene-based thermoplastic elastomers; and mixtures of two or more of them.

As shown in FIG. 4, the insertion part 37 is spaced apart from the inner periphery 23a of the female luer 23 in a state where the cap 14 is fixed (attached) to the female luer 23. That is, the outer diameter of the insertion part 37 is smaller than the inner diameter of the female luer 23, and therefore an annular gap 40 is created between the inner periphery 23a of the female luer 23 and the outer periphery of the insertion part 37. The annular gap 40 is in communication with the inside of the body part 20 of the barrel main body 12.

Further, in a state where the cap 14 is fixed (attached) to the female luer 23, the sealing part 39 is in close contact with the distal end surface (pressing part 28) of the female luer 23 along the entire circumference of the opening 23b of the female luer 23, and is dented in the distal direction by pressing with the pressing part 28 in the distal direction. It is to be noted that the sealing part 39 has a flat proximal end surface in its natural state (in a state where the sealing part 39 is not pressed with the pressing part 28).

The main body 34 of the cap 14 is made of a material harder than the elastic member 32 (e.g., a material mentioned above as an example of the constituent material of the barrel main body 12), and has a recess 42 opened in the proximal direction. Specifically, the main body 34 has a cap-side connector 44 that is threadedly engaged with the female luer-side connector 26, a supporting part 46 that supports the flange part 38 of the elastic member 32, an anti-rotation part 48 that prevents the relative rotation of the elastic member 32 with respect to the main body 34, and a cover 50 that covers the outer periphery of the female luer 23. It is to be noted that the outer periphery of the main body 34 has surface irregularities formed to prevent slipping at the time when the cap 14 is rotated.

The cap-side connector 44 is formed to project from the inner periphery of the cover 50. In this embodiment, the cap-side connector 44 is a female screw 45 that is threadedly engaged with the female luer-side connector 26 (see FIG. 5). The supporting part 46 is formed by the bottom of the recess 42, and the flange part 38 of the elastic member 32 is inserted and held in the supporting part 46. The flange part 38 has an outer diameter larger than the diameter of the outer periphery of the supporting part 46, and is fitted to the supporting part 46. This makes it possible to eliminate the necessity to integrally mold the elastic member 32 and the main body 34 or to fix the elastic member 32 to the main body 34 with an adhesive or the like and therefore to simplify a production process. The anti-rotation part 48 projects from the center of the bottom of the recess 42 in the proximal direction along the axis of the cap 14. The free end of the supporting part 46 (the proximal end of the cap 14) is positioned on the distal side of a proximal opening 34a of the main body 34.

It is to be noted that engagement (fixation) between the cap 14 and the female luer 23 is not limited to the above-described threaded engagement. For example, the cap-side connector 44 may be a cover-side engagement projection provided to project inward from the inner periphery of the cover 50, and the female luer-side connector 26 may be a female luer-side engagement projection provided to project outward from the outer periphery of the female luer 23 so that the cover-side engagement projection is caught on the proximal side of the female luer-side engagement projection. In this case, when the cap 14 is pulled in the distal direction, the cover 50 is elastically deformed and the cover-side engagement projection overpasses the female luer-side engagement projection so that the cap 14 can be separated from the female luer 23.

Figure 5:
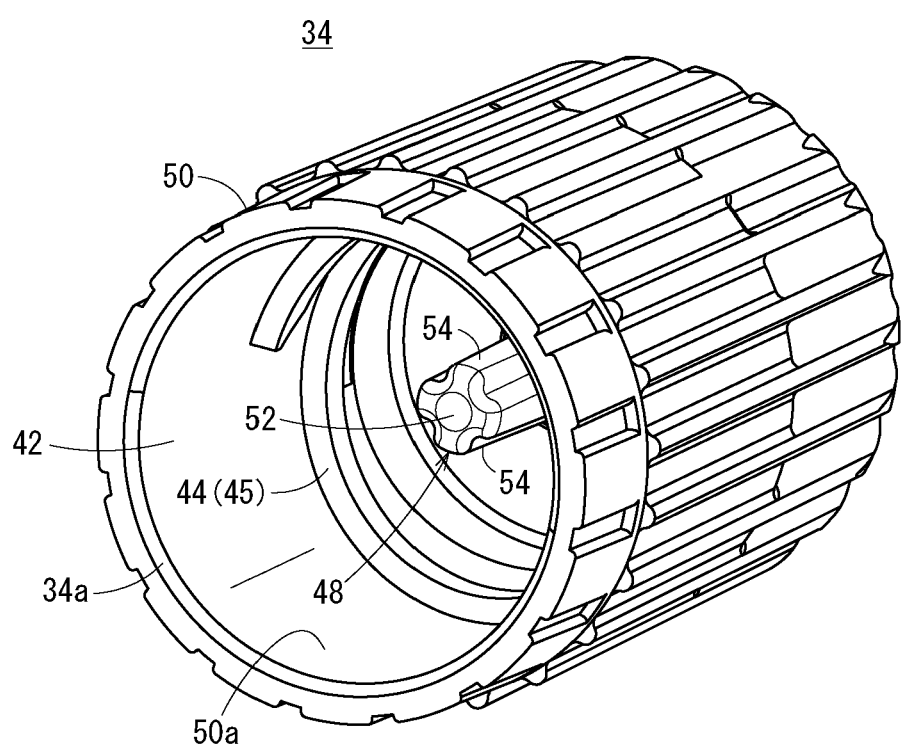
FIG. 5 is a perspective view of a main body of a cap viewed from the proximal end side of the main body.

The anti-rotation part 48 is inserted into the cylindrical part 36 of the elastic member 32 and engaged with the inner periphery 36a of the cylindrical part 36. Specifically, as shown in FIG. 5, the anti-rotation part 48 has a columnar part 52 that extends in the axial direction of the cap 14, and a plurality of ribs 54 that project outward from the outer periphery of the columnar part 52 and extend in the axial direction.

Figure 6:
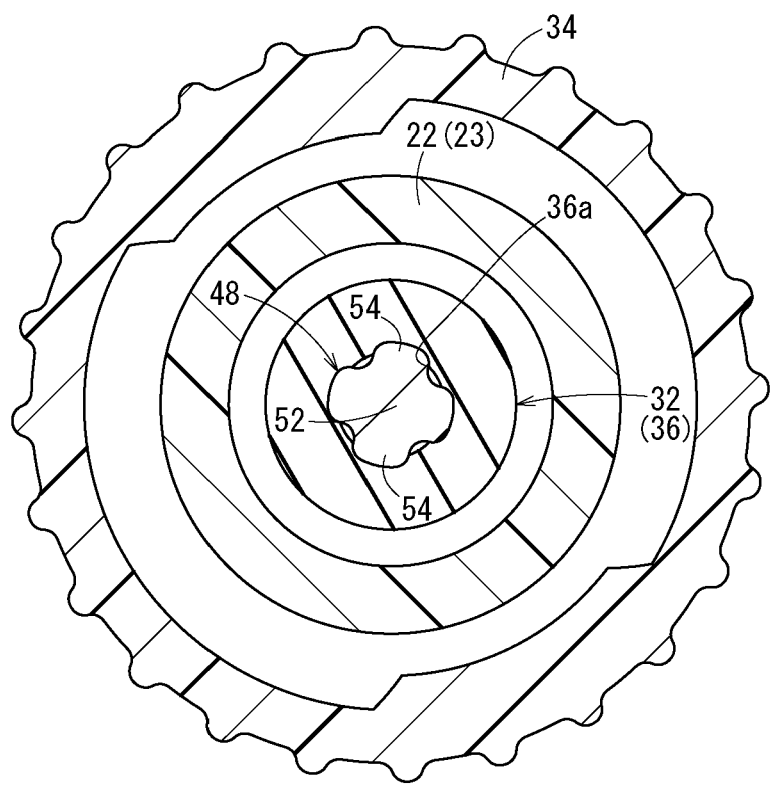
FIG. 6 is a cross-sectional view taken along the line VI-VI in FIG. 4.

The ribs 54 are provided at intervals on the outer periphery of the columnar part 52 in the circumferential direction. As shown in FIG. 6 that is a cross-sectional view taken along the line VI-VI in FIG. 4, the anti-rotation part 48 having the ribs 54 is fitted to the cylindrical part 36 in a state where the inner periphery 36a of the cylindrical part 36 of the elastic member 32 is elastically deformed by the anti-rotation part 48 so as to have surface irregularities. This makes it possible to prevent the relative rotation of the elastic member 32 with respect to the main body 34.

It is to be noted that the number of the ribs 54 provided on the columnar part 52 may be only one. Also in this case, the effect of preventing the relative rotation of the elastic member 32 with respect to the main body 34 can be obtained. Further, the inner periphery 36a of the cylindrical part 36 of the elastic member 32 may have one or more inner ribs that extend in the axial direction and radially project inward. When the number of the inner ribs is two or more, the inner ribs may be provided at intervals in the circumferential direction. In this case, the inner rib(s) of the elastic member 32 is(are) engaged with the ribs 54 of the columnar part 52, which makes it possible to further enhance the effect of preventing the relative rotation of the elastic member 32 with respect to the main body 34. The anti-rotation part 48 is not limited to one having the ribs 54, and may have any structure as long as its cross-section perpendicular to the axial direction has a non-circular profile. The anti-rotation part 48 whose cross-sectional profile is non-circular can prevent the relative rotation of the elastic member 32 with respect to the main body 34. Alternatively, the anti-rotation part 48 may be a rib formed on the inner periphery of the supporting part 46 to radially project inward. The anti-rotation part 48 is fitted to the flange part 38 in a state where the outer periphery of the flange part 38 of the elastic member 32 is elastically deformed by the rib so as to have surface irregularities. This makes it possible to prevent the relative rotation of the elastic member 32 with respect to the main body 34.

Alternatively, the inner periphery of the supporting part 46 and the outer periphery of the flange part 38 may have polygonal cross-sectional shapes that correspond with each other to prevent the relative rotation of the elastic member 32 with respect to the main body 34. In this case, the anti-rotation part 48 constitutes the inner periphery of the supporting part 46. Alternatively, the anti-rotation part 48 may be provided, at the distal end of the flange part 38, as a projection to be engaged with a recess provided at the bottom (distal end) of the supporting part 46. It is to be noted that in a case where the anti-rotation part 48 other than the columnar part 52 is provided, the columnar part 52 may be omitted from the main body 34.

As shown in FIG. 4, the cover 50 extends from a base 56 of the cap 14 in the proximal direction. In a state where the cap 14 is fixed to the female luer 23, the cover 50 covers almost the entire length of the female luer 23, and the proximal end of the cover 50 is in proximity to the distal end surface 20a of the body part 20 of the barrel main body 12. The cover 50 is thinner and is more likely to deform as compared to the female luer 23 having the projections 30.

An engagement force between the cover 50 and the projections 30 is larger than a disengagement force exerted on the cap 14 based on the elastic force of the elastic member 32 (specifically, the sealing part 39). In a state where the cap 14 is fixed to the female luer 23, a proximal-side inner periphery 50a of the cover 50 is engaged with the projections 30 provided in the female luer 23, which prevents the loosening of the cap 14.

Figure 7:
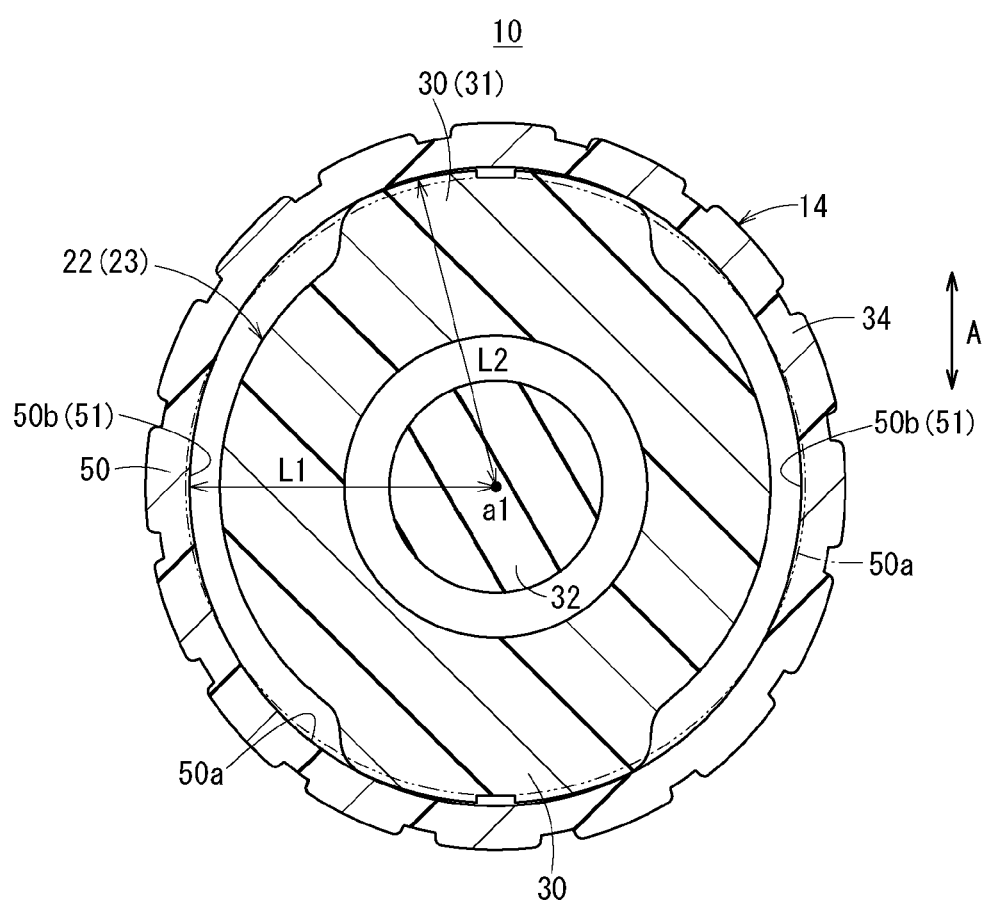
FIG. 7 is a cross-sectional view taken along the line VII-VII in FIG. 4.

As shown in FIG. 7 that is a cross-sectional view taken along the line VII-VII in FIG. 4, the proximal-side inner periphery 50a of the cover 50 has reduced radius portions 50b. A distance L1 from a rotation axis a1 of the cap 14 to each of the reduced radius portions 50b at the time when the cap 14 is threadedly engaged with the cylinder tip 22 is smaller than a distance L2 from the rotation axis a1 to the outer end of each of the projections 30. In this embodiment, the cross-sectional shape of the proximal-side inner periphery 50a of the cover 50 is not an accurate circle but an ellipse (an ellipse having a long axis in a direction represented by an arrow A in FIG. 7). Specifically, a part of the proximal-side inner periphery 50a of the cover 50 is radially expanded outward by the projections 30 provided in the female luer 23, and therefore the other part of the proximal-side inner periphery 50a is deformed inward so that the reduced radius portions 50b are formed. In this embodiment, the proximal-side inner periphery 50a of the cover 50 has a circular cross-section perpendicular to the axis of the cover 50 before the production of the syringe barrel 18, and therefore the reduced radius portions 50b are provided to be opposed to each other with respect to the rotation axis a1. Therefore, the proximal-side inner periphery 50a of the cover 50 has an elliptical cross-sectional shape.

That is, the proximal-side inner periphery 50a of the cover 50 has a circular (almost true circular) cross-sectional shape represented by a chain double-dashed line in FIG. 7 at the time when the main body 34 is produced. However, when the cap 14 is attached to the barrel main body 12 in the production process of the pre-filled syringe 10, the reduced radius portions 50b are provided so that the proximal-side inner periphery 50a of the cover 50 has an elliptical cross-sectional shape. As a result, a non-circular structure formed by the proximal-side inner periphery 50a of the cover 50 is engaged with a non-circular structure formed by the two projections 30, and therefore the function of preventing the loosening of the cap 14 with respect to the female luer 23 delivers. Specifically, the reduced radius portions 50b of the cover 50 are engaged with the projections 30 (female luer-side engagement part 31), and therefore the cap 14 is hard to loosen. That is, the reduced radius portions 50b constitute the cap-side engagement part 51 that is engaged with the female luer-side engagement part 31 in a state where the female luer-side connector 26 is threadedly engaged with the cap-side connector 44. Further, the pre-filled syringe 10 is subjected to autoclave sterilization in its production process in a state where the cap 14 is attached to the barrel main body 12. Therefore, the cap 14 is thermally deformed by high heat associated with autoclave sterilization so that the deformation of the proximal-side inner periphery 50a of the cover 50 by the projections 30 is established. As a result, the proximal-side inner periphery 50a of the cover 50 is more reliably provided with the reduced radius portions 50b and has an elliptical cross-sectional shape. It is to be noted that even when autoclave sterilization is not performed, deformation of the proximal-side inner periphery 50a of the cover 50 by the projections 30 is gradually established, and therefore the proximal-side inner periphery 50a of the cover 50 can be provided with the reduced radius portions 50b and has an elliptical cross-sectional shape.

An engagement force between the reduced radius portions 50b of the cover 50 and the projections 30 is larger than a disengagement force exerted on the cap 14 based on the elastic force of the elastic member 32 (specifically, the sealing part 39). This makes it possible to reliably prevent the loosening of the cap 14.

It is to be noted that the number of the projections 30 provided in the female luer 23 may be only one. Also in this case, the proximal-side inner periphery 50a of the cover 50 can have a non-circular cross-sectional shape during sterilization in the production process. The projections 30 may be arranged at, for example, 60° intervals. In this case, the proximal-side inner periphery 50a of the cover 50 can have a cross-sectional shape close to a triangle (a triangular cross-sectional shape having round corners) during sterilization in the production process. Alternatively, the projection 30 may be formed so that its outer edge has an elliptical shape surrounding the entire outer circumference of the female luer 23. In this case, the length of the short axis of the elliptical projection 30 is smaller than the diameter of the proximal-side inner periphery 50a of the cover 50, and the length of the long axis of the elliptical projection 30 is larger than the diameter of the proximal-side inner periphery 50a of the cover 50. This makes it possible to allow the proximal-side inner periphery 50a of the cover 50 to have an elliptical cross-sectional shape whose short and long axes correspond to those of the elliptical shape of the projection 30 to form reduced radius portions in the production process.

Next, the gasket 16 will be described with reference to FIG. 3. The gasket 16 is inserted into the barrel main body 12. The gasket 16 has a distal end surface 60, and the distal end surface 60 has a tapered shape that becomes thinner toward the distal end. The gasket 16 has two or more ring-shaped sealing projections (in FIG. 3, two ring-shaped sealing projections) 62 formed on its outer periphery at intervals in the axial direction. In a state where the gasket 16 is inserted in the barrel main body 12, the sealing projections 62 are in close contact with the inner periphery of the barrel main body 12. Therefore, the gasket 16 is liquid-tightly and slidably movable in the barrel main body 12.

The gasket 16 may have a coating film formed on its outer surface to reduce sliding resistance against the inner periphery of the barrel main body 12. Examples of such a coating film include fluorine-based resins such as polytetrafluoroethylene (PTFE), tetrafluoroethylene.perfluoroalkylvinyl ether copolymer resin (PFA), tetrafluoroethylene.hexafluoropropylene copolymer (FEP), polychlorotrifluoroethylene (PCTFE), and polyvinylidene fluoride (PVDF), polyparaxylylene, and diamond-like carbon.

Further, in order to reduce the sliding resistance of the gasket 16 against the barrel main body 12, the inner periphery of the barrel main body 12 or the outer periphery of the gasket 16 may be coated with a liquid lubricant (e.g., silicone oil).

The gasket 16 has a fitting recess 64 provided to have an opening at its proximal end. The fitting recess 64 has a male screw 66 formed on its inner periphery. The fitting recess 64 can be threadedly engaged with the distal end of a plunger not shown. Examples of a constituent material of the gasket 16 include those mentioned above as examples of the constituent material of the elastic member 32 of the cap 14.

It is to be noted that in the pre-filled syringe 10 according to this embodiment, a gasket stopper 68 is detachably attached to the proximal end (flange 24) of the barrel main body 12 to prevent the gasket 16 from coming out of the barrel main body 12 in the proximal direction. As shown in FIG. 2 and FIG. 3, the gasket stopper 68 has a stopper plate 72 having a communication path 70 that penetrates therethrough in the axial direction and has a diameter smaller than the inner diameter of the body part 20 of the barrel main body 12, and a semi-circular engagement plate 74 that is laterally opened to be engaged with the flange 24 of the barrel main body 12. The body part 20 of the barrel main body 12 is inserted into the engagement plate 74, and the flange 24 is inserted between the stopper plate 72 and the engagement plate 74 so that the gasket stopper 68 is attached to the proximal end of the barrel main body 12.

Next, the drug M will be described which is filled in the filling chamber 13 defined by the barrel main body 12, the gasket 16, and the cap 14. The drug M may be of any type, such as a powdered drug, a freeze-dried drug, a solid drug, or a liquid drug, as long as the drug M can be dissolved in or diluted with a medical liquid L (specifically, a solvent such as normal saline) filled in a dilution-side pre-filled syringe 80 (see FIG. 8B and FIG. 8C). Examples of the drug M include protein preparations, antitumor agents, vitamin preparations (multivitamin preparations), various amino acids, antithrombotic agents such as heparin, insulin, antibiotics, pain relievers, cardiotonic agents, intravenous anesthetics, medical anesthetics, antiparkinsonian agents, anti-ulcer agents, adrenal corticosteroids, and antiarrhythmic agents.

The syringe barrel 18 and the pre-filled syringe 10 according to the present embodiment basically have such structures as described above. Hereinbelow, their functions and effects will be described.

In the pre-filled syringe 10 equipped with the syringe barrel 18 having such a structure as described above, the gap 40 is provided between the inner periphery 23a of the female luer 23 and the insertion part 37 of the cap 14. Therefore, as will be described below, the inner periphery 23a of the female luer 23 can be sterilized.

In the production process of the pre-filled syringe 10, autoclave sterilization (high-pressure steam sterilization) is performed to achieve a predetermined cleanliness level. As one method of such sterilization, the pre-filled syringe 10 assembled as shown in FIG. 1 and FIG. 3 is subjected to sterilization. This makes it possible to sterilize the outer surface of the pre-filled syringe 10, the proximal end surface of the gasket 16 and the fitting recess 64, and the inner periphery of the barrel main body 12 located on the proximal side of the gasket 16 by exposure to high-temperature and high-pressure steam. Further, not only these areas but also the inner surface of the syringe constituting the filling chamber 13 is sterilized.

That is, since the filling chamber 13 is filled with the drug M, the inner surface of the syringe that is in contact with the drug M heated at high temperature associated with sterilization is sterilized. Further, even when a space not filled with the drug is present in the filling chamber 13, the inner surface of the syringe is sterilized with the steam of the drug M (in a case where the drug M is liquid). In this case, as shown in FIG. 4, since the annular gap 40 is created between the inner periphery 23a of the female luer 23 and the outer periphery of the insertion part 37 of the cap 14, the inner periphery 23a of the female luer 23 is effectively sterilized by the entry of the high-temperature drug M or the steam of the drug M into the gap 40.

As another method of the sterilization, the syringe barrel 18 is subjected to sterilization before the filling of the drug M and the insertion of the gasket 16. Specifically, the syringe barrel 18 is assembled by attaching the cap 14 to the barrel main body 12, and is then subjected to autoclave sterilization. In this case, since the annular gap 40 is created between the inner periphery 23a of the female luer 23 and the insertion part 37 of the cap 14, the inner periphery 23a of the female luer 23 is also effectively sterilized by the entry of high-temperature steam into the gap 40. Then, after the sterilization, the drug M is filled into the barrel main body 12 of the sterilized syringe barrel 18 in a sterilized space (e.g., in an isolator), and the gasket 16 is inserted into the barrel main body 12, and the gasket stopper 68 is finally attached. In this way, the pre-filled syringe 10 shown in FIG. 1 is completed.

The cross-sectional shape of the proximal-side inner periphery 50a of the cover 50 is formed by thermal deformation of the cover 50 caused by heat at the time of the above-described autoclave sterilization. That is, the cross-sectional shape of the proximal-side inner periphery 50a of the cover 50 before autoclave sterilization is a circle (almost true circle) as shown by a virtual line in FIG. 7. However, at the time of autoclave sterilization, the cover 50 that is thinner and is more likely to deform than the female luer 23 is softened by heat and thermally deformed in a state where the cover 50 receives a pressing force applied by the projections 30 outward in a direction represented by the arrow A. As a result, as shown in FIG. 7, the proximal-side inner periphery 50a of the cover 50 after sterilization has an elliptical cross-sectional shape fitted to the two projections 30 provided on the outer periphery of female luer 23. That is, irrespective to the positional relationship in the circumferential direction between the projections 30 and the cover 50, the projections 30 expand part of the cover 50 outward, and therefore the other part of the proximal-side inner periphery 50a is reliably deformed inward so that the reduced radius portions 50b are formed. Therefore the function of preventing the loosening of the cap 14 with respect to the female luer 23 delivers.

Next, a method for operating (using) the pre-filled syringe 10 will be described mainly with reference to FIG. 3 and FIGS. 8A to 8C. As shown in FIG. 3, the pre-filled syringe 10 before use is in a state where the cap 14 is attached to the female luer 23 of the barrel main body 12. In this case, in the pre-filled syringe 10, the sealing part 39 made of an elastic material is in close contact with the distal end surface of the female luer 23 along the entire circumference of the opening 23b, and therefore the opening 23b of the female luer 23 is liquid-tightly sealed. Further, the pressing part 28 provided at the distal end of the female luer 23 presses the sealing part 39 along the entire circumference of the opening 23b, and therefore the pressing part 28 and the sealing part 39 are in sufficiently close contact with each other so that excellent sealing performance is achieved.

In a state where the cap 14 is attached to the female luer 23, that is, in a state where the pressing part 28 presses the sealing part 39, a force to rotate the cap 14 in a direction to loosen the cap 14 is exerted based on the elastic force of the sealing part 39. If the cap 14 is loosened before the use of the pre-filled syringe 10, there is a possibility that the leakage of the drug M occurs. For this reason, this embodiment has a structure in which the projections 30 are provided on the outer periphery of a proximal end part of the female luer 23 to prevent the loosening of the cap 14 before use. That is, the reduced radius portions 50b of the main body 34 (cover 50) having a non-circular shape (elliptical shape) formed by thermal deformation at the time of sterilization are engaged with the projections 30 provided on the outer periphery of a proximal end part of the female luer 23 with high accuracy. Therefore, the loosening of the cap 14 before use is effectively prevented. Specifically, when the cap 14 is tried to be rotated in a direction to loosen threaded engagement between the cap 14 and the female luer 23 in the presence of the reduced radius portions 50b, resistance is generated to cause the reduced radius portions 50b to overpass the projections 30. As a result, the cap 14 is hard to loosen. In this way, the reduced radius portions 50b function as a loosening-resistance generator.

Figure 8A:
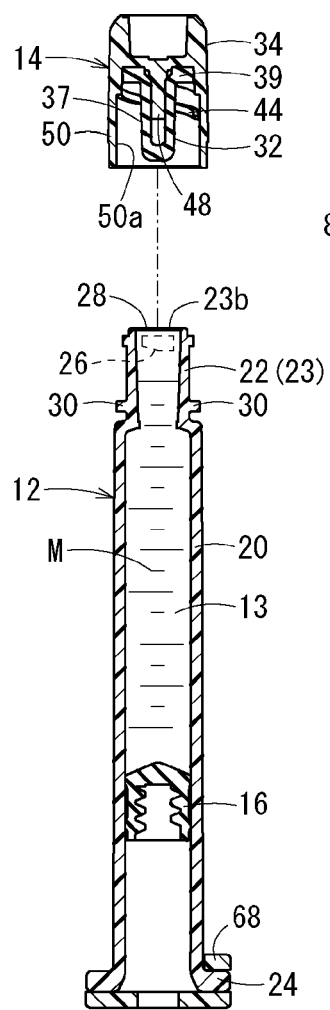
FIG. 8A is an explanatory diagram illustrating the operation of the pre-filled syringe shown in FIG. 1.

When the pre-filled syringe 10 is used, as shown in FIG. 8A, the cap 14 is opened. Specifically, in a state where the female luer 23 is directed upward, the cap 14 is rotated in a predetermined direction around the barrel main body 12 to release engagement (threaded engagement) between the cap-side connector 44 and the female luer-side connector 26 to remove the cap 14 from the female luer 23. In this case, when a torque equal to or larger than a predetermined torque is applied to the cap 14, the proximal side of the main body 34 (cover 50) is elastically deformed, which allows the cap 14 to be rotated and removed.

Particularly, in this embodiment, since the projections 30 are provided on the outer periphery of a proximal end part of the female luer 23, engagement between the projections 30 and the main body 34 is released only by slightly rotating the cap 14. That is, the projections 30 and the main body 34 are engaged only in the initial stage of the operation of opening the cap 14, and thereafter the cap 14 can be rotated with a little operating force thereafter. Therefore, the cap 14 is easily opened.

In this embodiment, since the cap 14 has the anti-rotation part 48, the elastic member 32 is rotated together with the main body 34 at the time of the operation of opening the cap 14. For this reason, the elastic member 32 is reliably separated from the pressing part 28 of the female luer 23 by rotating the cap 14. Therefore, the elastic member 32 does not remain on the female luer 23 side due to sticking to the pressing part 28 of the female luer 23.

Figure 8B:
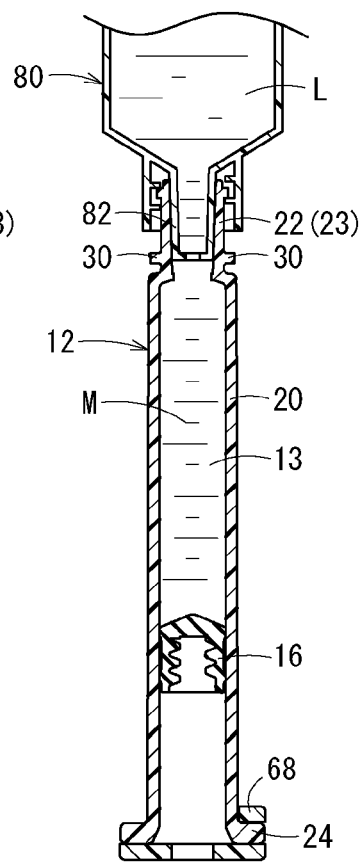
FIG. 8B is an operating explanatory diagram following FIG. 8A.

After the cap 14 is removed from the female luer 23, as shown in FIG. 8B, the pre-filled syringe 80 filled with the medical liquid L is connected to the pre-filled syringe 10. Specifically, the male luer 82 provided as a cylinder tip in the pre-filled syringe 80 is inserted into and connected to the female luer 23 of the pre-filled syringe 10. In this case, since a space corresponding to the volume of the male luer 82 is previously provided by inserting the cylindrical part 36 (insertion part 37) of the elastic member 32 into the female luer 23 in a state where the cap 14 is not opened, the drug M does not leak from the barrel main body 12 at the time when the male luer 82 is connected.

The medical liquid L filled in the pre-filled syringe 80 may be a liquid for dissolving a drug, such as distilled water for injection or normal saline, or a liquid drug that contains a drug (e.g., a vitamin preparation or a mineral) and can dissolve or dilute the drug M filled in the pre-filled syringe 10. It is to be noted that the medical liquid L is not limited to one previously filled in the pre-filled syringe 80. Rather, the medical liquid may be sucked into an empty syringe from a vial or the like in a necessary amount when required.

Figure 8C:
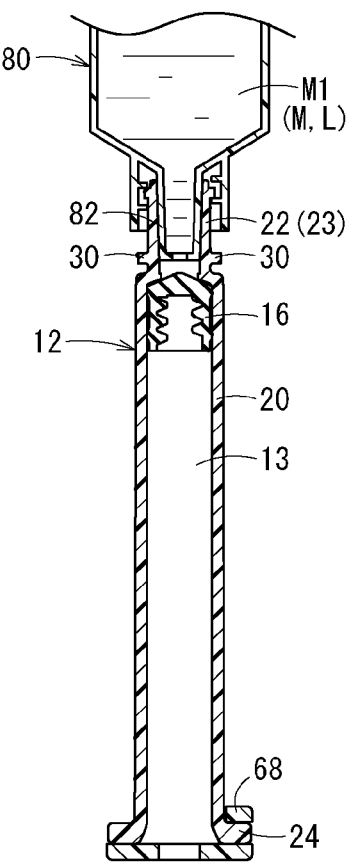
FIG. 8C is an operating explanatory diagram following FIG. 8B.

Then, as shown in FIG. 8C, a plunger (not shown) of the pre-filled syringe 80 is pulled in the proximal direction to suck the drug M from the barrel main body 12 into the pre-filled syringe 80 so that the drug M is mixed with and dissolved in or diluted with the medical liquid L in the pre-filled syringe 80. This makes it possible to prepare a desired liquid drug M1. It is to be noted that in order to promote the dissolution or dilution of the drug M, so-called pumping may be performed in such a manner that the drug M is once sucked into the pre-filled syringe 80, and then the resulting mixture is returned to the barrel main body 12 and again sucked into the pre-filled syringe 80. In this case, since the gasket stopper 68 is attached to the proximal end (flange 24) of the barrel main body 12, the gasket 16 does not come out of the barrel main body 12 in the proximal direction, which makes it possible to prevent the leakage of the mixture from the proximal end of the barrel main body 12. Further, since the gasket stopper 68 has the communication path 70 formed to penetrate therethrough in the axial direction, the inside of the barrel main body 12 located on the proximal side of the gasket 16 and the outside of the barrel main body 12 communicate with each other. Therefore, the sliding of the gasket 16 in the barrel main body 12 during pumping is not interfered with. It is to be noted that the communication path 70 is not limited to a hole penetrating through the gasket stopper 68 in the axial direction as long as the communication path 70 allows the inside of the barrel main body 12 located on the proximal side of the gasket 16 and the outside of the barrel main body 12 to communicate with each other. For example, a projection may be formed on the distal end surface of the stopper plate 72 of the gasket stopper 68 to provide, as the communication path 70, a gap between the stopper plate 72 and the proximal end surface of the barrel main body 12.

As has been described above, in the syringe barrel 18 and the pre-filled syringe 10 according to this embodiment, the gap 40 is provided between the inner periphery 23a of the female luer 23 and the insertion part 37, which makes it possible to sterilize the inner periphery 23a of the female luer 23. More specifically, when the syringe barrel 18 is subjected to sterilization in its production process, high-temperature steam or liquid comes into contact with the inner periphery 23a of the female luer 23, which makes it possible to sterilize the inner periphery 23a. Further, the insertion part 37 of the cap 14 is inserted into the female luer 23, which prevents the leakage of the drug M at the time when the male luer 82 is connected.

Further, this embodiment, the opening 23b of the female luer 23 is liquid-tightly sealed not by close contact between the inner periphery 23a of the female luer 23 and the outer periphery of the insertion part 37 but by close contact between the sealing part 39 and the distal end surface of the female luer 23 along the entire circumference of the opening 23b. Therefore, the syringe barrel 18 according to this embodiment can ensure liquid tightness at the time when the cap is not opened, can prevent the leakage of the drug at the time when the male luer is connected, and can sterilize the inner periphery 23a of the female luer 23.

Further, in this embodiment, since the pressing part 28 presses the sealing part 39 along the entire circumference of the opening 23b, the pressing part 28 and the sealing part 39 are in sufficiently close contact with each other so that excellent sealing performance is achieved. Further, this embodiment, since the insertion part 37 and the sealing part 39 are integrally formed as the elastic member 32, only one portion is required to be sealed, and therefore excellent sealing performance can be achieved by a simple structure.

In this embodiment, the main body 34 of the cap 14 has the anti-rotation part 48 that prevents the relative rotation of the elastic member 32 with respect to the main body 34. This structure makes it possible to, when the cap 14 is rotated and removed from the female luer 23, prevent the elastic member 32 from remaining on the female luer 23 side due to sticking to the pressing part 28. Further, since the anti-rotation part 48 is inserted into the cylindrical part 36 and engaged with the inner periphery 36a of the cylindrical part 36, the relative rotation of the elastic member 32 with respect to the main body 34 can be effectively prevented by a simple structure, and in addition, the anti-rotation part 48 can stably support the elastic member 32.

In this embodiment, since the anti-rotation part 48 has the columnar part 52 that extends along the axial direction of the cylindrical part 36 and the ribs 54 that project from the outer periphery of the columnar part 52 outward and extend in the axial direction, the relative rotation of the elastic member 32 with respect to the main body 34 can be more effectively prevented.

Further, in this embodiment, since the female luer 23 is provided with the female luer-side engagement part 31, and the cap 14 is provided with the cap-side engagement part 51 (see FIG. 7), the loosening of the cap 14 can be appropriately prevented. Particularly, in this embodiment, since the cap-side engagement part 51 is formed at the proximal end part of the cover 50, and the female luer 23 has the projections 30 that are formed to radially project from the outer periphery of a proximal end part of the female luer 23 and constitute the female luer-side engagement part 31, engagement between the projections 30 and the cover 50 is released only by slightly rotating the cap 14, and therefore the cap 14 can be easily opened.

Further, in this embodiment, since the reduced radius portions 50b of the cover 50 that are engaged with the projections 30 to prevent the loosening of the cap 14 are obtained as a result of deformation caused by a force received from the projections 30, the projections 30 and the cover 50 are engaged with each other in an accurate positional relationship. Therefore, it is not necessary to align a threaded engagement structure between the cap 14 and the cylinder tip 22 with the projections 30, and therefore it is possible to easily obtain a rattle-free structure for preventing the loosening of the cap 14.

Further, in this embodiment, the two projections 30 are provided which project in opposite directions with respect to the axis of the female luer 23. In this structure, the projections 30 are engaged with the cover 50 at two points opposite to each other, which is highly effective at preventing the loosening of the cap 14 and makes it possible to hold the cap 14 coaxially with the female luer 23.

Embodiments of the present invention have been described above, but the present invention is not limited to the above-described embodiments. Various changes may be made without departing from the scope of the present invention.

Further, the cap-side engagement part 51 and the female luer-side engagement part 31 are not limited to those of the above-described embodiment as long as the loosening of the cap 14 threadedly engaged with the female luer 23 can be prevented. For example, a loosening-preventing projection may be formed in the groove of the female screw 45 of the cap 14, which is engaged with the engagement projections constituting the female luer-side connector 26 when the cap-side connector 44 and the female luer-side connector 26 are threadedly engaged with each other. In this case, the cap-side engagement part 51 and the female luer-side engagement part 31 are constituted from the loosening-preventing projection and the engagement projections, respectively. Further, the cap-side engagement part 51 may be a groove or projection formed in or on the proximal-side inner periphery 50a of the cover 50, and the female luer-side engagement part 31 may be a projection that is formed to radially project from the outer periphery of a proximal end part of the female luer 23 so as to be engaged with the proximal-side groove or projection of the cover 50. Further, the cap-side engagement part 51 may be a recess or projection formed in or on the proximal-side inner periphery 50a of the cover 50, and the female luer-side engagement part 31 may be a projection that is formed to radially project from the outer periphery of a proximal end part of the female luer 23 so as to be engaged with the recess or projection of the proximal-side inner periphery 50a of the cover 50. Further, the cap-side engagement part 51 may be a recess or projection formed in or on the proximal end surface of the cover 50, and the female luer-side engagement part 31 may be a projection that is formed to radially project from the outer periphery of a proximal end part of the female luer 23 so as to be engaged with the recess or projection of the proximal end surface of the cover 50.

The invention claimed is:

1. A syringe barrel comprising:
a barrel main body having a female luer at a distal end of the barrel main body, the female luer being configured such that a male luer is insertable into and connectable to the female luer; and
a cap that is detachably attached to the female luer to close an opening of the female luer,
wherein the female luer has a female luer-side connector, and the cap is detachably attached to the female luer via the female luer-side connector,
wherein the cap includes an insertion part inserted into the female luer, a sealing part that seals the opening of the female luer, and a cap-side connector that is detachably engaged with the female luer-side connector, and
wherein, when the cap is fixed to the female luer by engagement between the female luer-side connector and the cap-side connector, the insertion part is spaced apart from an inner periphery of the female luer so as to create an annular gap between the inner periphery of the female luer and an outer periphery of the insertion part, the annular gap extending substantially entirely along a length of the insertion part and communicating with an inside of the barrel main body, and the sealing part is in contact with a distal end surface of the female luer along an entire circumference of the opening of the female luer.

2. The syringe barrel according to claim 1, wherein: the cap includes:
an elastic member including the sealing part, and
a cap main body that supports the elastic member, has the cap-side connector, and is harder than the elastic member, and
the female luer includes a pressing part at a distal end of the female luer, the pressing part projecting in a distal direction such that, when the cap is fixed to the female luer, the pressing part presses against the sealing part along the entire circumference of the opening of the female luer.

3. The syringe barrel according to claim 2, wherein:
the elastic member includes the insertion part,
the insertion part is cylindrical and has a closed proximal end and a distal end opening, and
the sealing part includes a flange that surrounds the distal end opening of the insertion part.

4. The syringe barrel according to claim 2, wherein the female luer-side connector and the cap-side connector are threadedly engaged with each other.

5. The syringe barrel according to claim 4, wherein the cap main body has an anti-rotation part that prevents relative rotation of the elastic member with respect to the cap main body.

6. The syringe barrel according to claim 5, wherein the anti-rotation part is inserted into the insertion part and engaged with an inner periphery of the insertion part.

7. The syringe barrel according to claim 6, wherein the anti-rotation part has a columnar part that extends along an axial direction of the cap and a rib that projects from an outer periphery of the columnar part outward and extends in the axial direction.

8. The syringe barrel according to claim 4, wherein:
the cap main body has a cap-side engagement part, and
the female luer has a female luer-side engagement part that is engaged with the cap-side engagement part to prevent loosening of the cap when the female luer-side connector and the cap-side connector are threadedly engaged with each other.

9. The syringe barrel according to claim 8, wherein an engagement force between the cap-side engagement part and the female luer-side engagement part is larger than a disengagement force exerted on the cap based on an elastic force of the elastic member.

10. The syringe barrel according to claim 8, wherein:
the cap main body includes a cylindrical cover that covers an outer periphery of the female luer,
the cap-side engagement part is formed at a proximal end part of the cover, and
the female luer-side engagement part comprises at least one projection that radially projects from an outer periphery of a proximal end part of the female luer.

11. The syringe barrel according to claim 10, wherein:
a proximal-side inner periphery of the cap-side engagement part comprises a reduced radius portion, and, when the cap is threadedly engaged with the female luer, a distance from a rotation axis of the cap to the reduced radius portion is smaller than a distance from the rotation axis to an outer end of the at least one projection, and
a portion of the proximal-side inner periphery of the cover is expanded outwardly by the at least one projection, which deforms another portion of the proximal-side inner periphery inwardly, thereby forming the reduced radius portion, and
the reduced radius portion is engaged with the at least one projection to prevent loosening of the cap when the cap is attached to the female luer.

12. A pre-filled syringe comprising:
the syringe barrel according to claim 1;
a gasket that is slidably movable in the barrel main body in a liquid-tight manner; and
a drug filled in a filling chamber defined by the barrel main body, the gasket, and the cap.

13. A syringe barrel comprising:
a barrel main body having a female luer at a distal end of the barrel main body, the female luer being configured such that a male luer is insertable into and connectable to the female luer; and
a cap that is detachably attached to the female luer to close an opening of the female luer,
wherein the female luer has a female luer-side connector, and the cap is detachably attached to the female luer via the female luer-side connector, wherein the cap includes an insertion part inserted into the female luer, a sealing part that seals the opening of the female luer, and a cap-side connector that is detachably engaged with the female luer-side connector, wherein, when the cap is fixed to the female luer by engagement between the female luer-side connector and the cap-side connector, the insertion part is spaced apart from an inner periphery of the female luer, and the sealing part is in contact with a distal end surface of the female luer along an entire circumference of the opening of the female luer, and wherein the anti-rotation part has a columnar part that extends along an axial direction of the cap and a rib that projects from an outer periphery of the columnar part outward and extends in the axial direction.

14. A syringe barrel comprising:

a barrel main body having a female luer at a distal end of the barrel main body, the female luer being configured such that a male luer is insertable into and connectable to the female luer; and a cap that is detachably attached to the female luer to close an opening of the female luer, wherein the female luer has a female luer-side connector, and the cap is detachably attached to the female luer via the female luer-side connector, wherein the cap includes an insertion part inserted into the female luer, a sealing part that seals the opening of the female luer, and a cap-side connector that is detachably engaged with the female luer-side connector, wherein, when the cap is fixed to the female luer by engagement between the female luer-side connector and the cap-side connector, the insertion part is spaced apart from an inner periphery of the female luer so as to create an annular gap communicating with an inside of the barrel main body between the inner periphery of the female luer and an outer periphery of the insertion part, and the sealing part is in contact with a distal end surface of the female luer along an entire circumference of the opening of the female luer, and wherein the insertion part and the sealing part are configured to be detached from the female luer as a unitary member during removal of the cap from the female luer.

* * * * *